(12) United States Patent
Ding et al.

(10) Patent No.: US 12,285,529 B2
(45) Date of Patent: Apr. 29, 2025

(54) METHOD FOR PREPARING PROBIOTIC-LOADED MICROCAPSULE, PRODUCT OBTAINED FROM THE SAME, AND USE OF THE SAME

(71) Applicants: National Institute for Nutrition and Health Chinese Center for Disease Control and Prevention, Xicheng District (CN); Institute of Process Engineering, Chinese Academy of Sciences, Haidian District (CN)

(72) Inventors: Gangqiang Ding, Xicheng District (CN); Junsheng Huo, Xicheng District (CN); Lianyan Wang, Haidian District (CN); Jian Huang, Xicheng District (CN); Guifeng Zhang, Haidian District (CN); Yanbin Tang, Xicheng District (CN); Ke Cao, Haidian District (CN); Yingbin Cui, Haidian District (CN); Zheng Cao, Haidian District (CN)

(73) Assignee: NATIONAL INSTITUTE FOR NUTRITION AND HEALTH CHINESE CENTER FOR DISEASE CONTROL AND PREVENTION, Beijing (CN)

( * ) Notice: Subject to any disclaimer, the term of this patent is extended or adjusted under 35 U.S.C. 154(b) by 1050 days.

(21) Appl. No.: 17/264,515

(22) PCT Filed: Aug. 18, 2020

(86) PCT No.: PCT/CN2020/109716
§ 371 (c)(1),
(2) Date: Jan. 29, 2021

(87) PCT Pub. No.: WO2021/088460
PCT Pub. Date: May 14, 2021

(65) Prior Publication Data
US 2022/0142933 A1    May 12, 2022

(30) Foreign Application Priority Data

Nov. 5, 2019  (CN) .......................... 201911072088.7

(51) Int. Cl.
*A61K 9/50*      (2006.01)
*A23L 29/256*    (2016.01)
(Continued)

(52) U.S. Cl.
CPC .......... *A61K 9/5036* (2013.01); *A23L 29/256* (2016.08); *A23L 33/135* (2016.08);
(Continued)

(58) Field of Classification Search
None
See application file for complete search history.

(56) References Cited

U.S. PATENT DOCUMENTS

| 2003/0165472 | A1* | 9/2003 | McGrath | .................. A01K 7/02 424/93.4 |
| 2011/0159152 | A1 | 6/2011 | Masato et al. | |

FOREIGN PATENT DOCUMENTS

| CN | 1969889 | 5/2007 |
| CN | 101289648 | 10/2008 |

(Continued)

OTHER PUBLICATIONS

English language translation of CN 101289648 A, Publ. Oct. 22, 2008. (Year: 2008).*

(Continued)

*Primary Examiner* — Dominic Lazaro
(74) *Attorney, Agent, or Firm* — Woodard, Emhardt, Henry, Reeves & Wagner, LLP

(57) ABSTRACT

The present application provides a method for preparing a probiotic-loaded microcapsule including: (1) dissolving sodium alginate in a solvent to obtain a sodium alginate
(Continued)

solution; (2) evenly mixing a probiotic with the sodium alginate solution obtained in step (1) to obtain a probiotic suspension; and (3) spraying the probiotic suspension obtained in step (2) into a salt solution, stirring and curing, to obtain the probiotic-loaded microcapsule. The microcapsule is prepared by a spraying method in conjunction with an ion curing method by using sodium alginate as the wall material of the microcapsule, so that the prepared microcapsule has a good spherical shape, a small particle size, good dispersibility and high pH sensitivity, forms a denser surface under an acidic condition to effectively protect probiotics, and can meet requirements for subsequent in vivo animal evaluations.

15 Claims, 10 Drawing Sheets

(51) Int. Cl.
    *A23L 33/135*     (2016.01)
    *A23P 10/30*     (2016.01)
    *A61K 35/745*     (2015.01)
    *A61K 35/747*     (2015.01)

(52) U.S. Cl.
    CPC ............ *A23P 10/30* (2016.08); *A61K 35/745* (2013.01); *A61K 35/747* (2013.01)

(56) References Cited

FOREIGN PATENT DOCUMENTS

| | | | |
|---|---|---|---|
| CN | 101289648 A | * | 10/2008 |
| CN | 101724622 | | 6/2010 |
| CN | 101856604 | | 10/2010 |
| CN | 102228235 | | 11/2011 |
| CN | 106418547 | | 2/2017 |
| CN | 106617093 | | 5/2017 |
| CN | 106993813 | | 8/2017 |
| CN | 108669298 | | 10/2018 |
| CN | 109156686 | | 1/2019 |
| CN | 109619593 | | 4/2019 |
| CN | 109700781 | | 5/2019 |
| CN | 110946287 | | 4/2020 |
| WO | WO 2015/019307 | | 2/2015 |

OTHER PUBLICATIONS

English language translation of CN 101289648 A. (Year: 2008).*
Varshney, D. & Singh, M., Lyophilized Biologics and Vaccines, Modality-Based Approaches, 2015, Springer New York Heidelberg Dordrecht London. (Year: 2015).*
Enterococcus faecium, Wikipedia; accessed at https://en.wikipedia.org/wiki/Enterococcus_faecium on Apr. 20, 2024. (Year: 2024).*
International Serach Report for PCT/CN2020/109716 mailed Nov. 9, 2020.
Office Action in related CN201911072088.7 dated Feb. 14, 2022.

* cited by examiner

METHOD FOR PREPARING PROBIOTIC-LOADED MICROCAPSULE, PRODUCT OBTAINED FROM THE SAME, AND USE OF THE SAME

TECHNICAL FIELD

The present application belongs to the field of microorganisms and, in particular, to a method for preparing a probiotic-loaded microcapsule, a product obtained from the same, and use of the same.

BACKGROUND

Probiotics are active microorganisms that can improve the intestinal microecological balance of a host and are beneficial to the host. The probiotics are colonized in the intestines and reproductive system of a human and can produce definite health effects. A certain number of probiotics ingested into a human body will produce many health promoting effects, such as controlling intestinal infections, enhancing immunity, regulating plasma and cholesterol levels, and providing anti-cancer effects. The probiotics can promote the utilization of lactose in patients with lactose intolerance. In recent years, more and more studies have proved that the probiotics can inhibit the growth of pathogenic bacteria, eliminate carcinogenic factors, and maintain normal intestinal flora, and have important physiological effects such as alleviating lactose intolerance, decreasing cholesterol, and improving immunity. A lack of probiotics will lead to adverse effects such as dysbiosis of intestinal flora, growth of spoilage bacteria, weakened intestinal peristalsis, low immune functions, and decreased synthesis of B vitamins.

When taken orally, many probiotics are prone to be inactivated by the strong acid environment in stomach and thus have lower activity in the intestines. To maximize the activity of the probiotics in the intestines and exert the beneficial effect of the probiotics in regulating the intestinal flora, the probiotics may be microencapsulated to be isolated and protected well, so that the probiotics can achieve better effects when reaching the intestines. *Lactobacillus acidophilus* in the genus *Lactobacillus* is a gram positive bacillus widely present in the intestines of humans and some animals.

CN104911171A has disclosed a method for preparing a probiotic microcapsule by compounding sodium alginate, gelatin and attapulgite. The method includes: purifying the attapulgite; mixing the attapulgite with the sodium alginate and the gelatin to afford a complex wall material; evenly mixing a prepared probiotic bacterium suspension with the complex wall material under certain conditions; slowly adding dropwise the resultant mixture into $CaCl_2$, curing and shaping; finally, drying by a vacuum-freezing method, to obtain the probiotic microcapsule. The substance embedded in the probiotic microcapsule prepared by this method has relatively low activity and a relatively low survival rate.

CN102228235A has disclosed a method for preparing a probiotic microcapsule and an application thereof, comprising isovolumetrically mixing a sodium alginate solution with a modified starch solution; then mixing with probiotics; spraying a $CaCl_2$ solution through a nozzle of a sprayer; allowing the mixture to stand and cure; and washing the resultant product with normal saline, and filtering. Although this method enhances the mechanical strength of the capsule wall to a certain extent, the size of the obtained capsule is difficult to control, and thus the method is difficult to be applied to the industrial production of food and medicine. Moreover, the addition of the modified starch weakens the pH-sensitive release characteristic of the microcapsule, so that some microcapsules cannot form dense surfaces in the acid environment of the stomach when immersed in the stomach and cannot quickly disintegrate in the weak acid environment of the intestines to release the embedded probiotics.

Therefore, it is an urgent problem to be solved in the art to develop a method for preparing a probiotic-loaded microcapsule that can maintain the activity of the embedded substance and easily release the embedded substance.

SUMMARY

The present application provides a method for preparing a probiotic-loaded microcapsule, a product obtained from the same, and use of the same. The probiotic-loaded microcapsule prepared by the method have the advantages of a good spherical shape, a controlled particle size, good dispersibility, good pH sensitivity, and ease to release in the intestines, and can meet requirements for subsequent in vivo animal evaluations.

In a first aspect, the present application provides a method for preparing a probiotic-loaded microcapsule, including the following steps:
(1) dissolving sodium alginate in a solvent to obtain a sodium alginate solution;
(2) evenly mixing a probiotic with the sodium alginate solution obtained in step (1) to obtain a probiotic suspension; and
(3) spraying the probiotic suspension obtained in step (2) into a salt solution, stirring and curing, to obtain the probiotic-loaded microcapsule.

The present application uses sodium alginate as a wall material of the probiotic microcapsule. With good biocompatibility and biodegradability, sodium alginate can absorb water in the presence of some divalent cations such as calcium and barium to form gel and thus be used for preparing microcapsules. In addition, alginate microcapsules have excellent pH-sensitive release characteristics. They form denser surfaces in an acidic environment to protect the embedded probiotics, and can quickly disintegrate in the pH environment of the intestines to release the embedded probiotics, thereby regulating the intestinal flora. The spray drying method is most widely used and has the advantages of simple operations and lower costs. The method of the present application prepares the microcapsule by a spraying method in conjunction with an ion curing method by using sodium alginate as the wall material of the microcapsule. Through the synergistic effects between these two methods, the microcapsule has a good spherical shape, a controlled particle size, and good dispersibility, and can meet requirements for subsequent in vivo animal evaluations through.

In an embodiment, the solvent in step (1) is water and/or an aqueous sodium chloride solution, preferably an aqueous sodium chloride solution.

In an embodiment, the aqueous sodium chloride solution has a concentration of 0.85% to 0.9% by mass, which may be, for example, 0.85%, 0.86%, 0.87%, 0.88%, 0.89%, or 0.9%.

In a specific embodiment, the solvent in step (1) is normal saline.

In an embodiment, the sodium alginate solution in step (1) has a concentration of 0.5% to 3% by mass, which may be, for example, 0.5%, 0.6%, 0.7%, 0.8%, 0.9%, 1%, 1.2%, 1.4%, 1.6%, 1.8%, 1.9%, 2%, 2.2%, 2.4%, 2.6%, 2.8% or 3%.

In an embodiment, the probiotic in step (2) is added in an amount of $10^8$-$10^{11}$ CFU/mL, which may be, for example, $1\times10^8$ CFU/mL, $2\times10^8$ CFU/mL, $3\times10^8$ CFU/mL, $4\times10^8$ CFU/mL, $5\times10^8$ CFU/mL, $6\times10^8$ CFU/mL, $7\times10^8$ CFU/mL, $8\times10^8$ CFU/mL, $9\times10^8$ CFU/mL, $1\times10^9$ CFU/mL, $2\times10^9$ CFU/mL, $3\times10^9$ CFU/mL, $4\times10^9$ CFU/mL, $5\times10^9$ CFU/mL, $6\times10^9$ CFU/mL, $7\times10^9$ CFU/mL, $8\times10^9$ CFU/mL, $9\times10^9$ CFU/mL, $1\times10^{19}$ CFU/mL, $2\times10^{19}$ CFU/mL, $3\times10^{19}$ CFU/mL, $4\times10^{19}$ CFU/mL, $5\times10^{19}$ CFU/mL, $6\times10^{19}$ CFU/mL, $7\times10^{19}$ CFU/mL, $8\times10^{19}$ CFU/mL, $9\times10^{19}$ CFU/mL or $1\times10^{11}$ CFU/mL.

In an embodiment, the probiotic in step (2) is selected from any one or a combination of at least two of *Lactobacillus acidophilus, Bifidobacterium* or gram-positive cocci.

In an embodiment, in step (3), the probiotic suspension is sprayed into the salt solution through a nozzle of a spray dryer.

In an embodiment, the salt solution is a calcium salt solution.

In an embodiment, the calcium salt solution has a concentration of 0.5-1.5 mol/L, which may be, for example, 0.5 mol/L, 0.6 mol/L, 0.7 mol/L, 0.8 mol/L, 0.9 mol/L, 1 mol/L, 1.1 mol/L, 1.2 mol/L, 1.3 mol/L, 1.4 mol/L or 1.5 mol/L.

In an embodiment, the calcium salt solution includes any one or a combination of at least two of calcium gluconate, calcium hydrogen phosphate, calcium lactate, calcium sulfate or calcium chloride, preferably calcium chloride.

In an embodiment, the probiotic suspension is sprayed into the ion solution at a gas velocity of 450-550 L/h, which may be, for example, 450 L/h, 460 L/h, 470 L/h, 480 L/h, 490 L/h, 500 L/h, 510 L/h, 520 L/h, 530 L/h, 540 L/h or 550 L/h.

In an embodiment, the feed rate of the spray dryer is 1-3 mL/min, and may be, for example, 1 mL/min, 1.2 mL/min, 1.4 mL/min, 1.6 mL/min, 1.8 mL/min, 2 mL/min, 2.2 mL/min, 2.4 mL/min, 2.6 mL/min, 2.8 mL/min or 3 mL/min.

The present application provides a process for preparing calcium alginate microcapsules which improves the embedding rate and gastrointestinal sensitive release of microcapsules. The process, through controlling the gas velocity at which the wall material suspension containing core materials is sprayed and the feed rate of the spray device during the formation of microcapsules, further improves the embedding rate of microcapsules. Moreover, the prepared calcium alginate microcapsules form dense protective layers in the acidic environment of the stomach so as not to release the embedded materials, and allow crosslinked valence bonds of calcium ions to be quickly dissociated in the neutral or weakly alkaline intestines to release the core materials embedded in the microcapsules, so that the microcapsules have a good pH-sensitive release behavior. In addition, the capsule size can be controlled by selecting the size of the nozzle and controlling the spraying process, further improving the overall performance of the microcapsule.

In an embodiment, after step (3), the method further includes step (4): washing the probiotic-loaded microcapsule obtained in step (3), collecting, and suspending and storing the probiotic-loaded microcapsule in a solvent.

In an embodiment, the probiotic-loaded microcapsule is washed by centrifugation.

In an embodiment, the solvent in step (4) is normal saline.

In a specific embodiment, the method includes the following steps:

(1) dissolving sodium alginate in a solvent to obtain a sodium alginate solution with a concentration of 0.5% to 3% by mass;

(2) evenly mixing a probiotic with the sodium alginate solution obtained in step (1) to obtain a probiotic suspension, wherein the probiotic is added in an amount of $10^8$-$10^{11}$ CFU/mL;

(3) spraying the probiotic suspension obtained in step (2) into a calcium salt solution through a nozzle of a spray device at a gas velocity of 450-550 L/h, stirring and curing, to obtain the probiotic-loaded microcapsule, wherein the calcium salt solution has a concentration of 0.5-1.5 mol/L, and the feed rate of the spray dryer is 1-3 mL/min; and (4) washing the probiotic-loaded microcapsule obtained in step (3) by centrifugation, collecting, suspending, and storing the probiotic-loaded microcapsule in normal saline.

In a second aspect, the present application provides a probiotic-loaded microcapsule prepared by the method for preparing a probiotic-loaded microcapsule described in the first aspect.

In an embodiment, the microcapsule has a particle size of 25-40 μm, which may be, for example, 25 μm, 26 μm, 27 μm, 28 μm, 29 μm, 30 μm, 31 μm, 32 μm, 34 μm, 35 μm, 36 μm, 37 μm, 38 μm, 39 μm or 40 μm.

In a specific embodiment, the microcapsule has a particle size of 30-35 μm.

In a third aspect, the present application provides use of the probiotic-loaded microcapsule described in the second aspect, for preparing health foods, beverages and foods, clinical nutritional preparations, pharmaceutical microcapsules or cosmetics.

Compared with the existing art, the present application has beneficial effects below.

(1) The method for preparing a probiotic-loaded microcapsule of the present application solves the problems where probiotic microcapsules prepared by traditional methods have large particle sizes, irregular spherical shapes, poor dispersibility and high costs, and are complicated to be prepared.

(2) The probiotic microcapsules of the present application have a particle size of 25-40 μm and good pH sensitivity, can form denser surfaces in the acidic environment to protect the embedded probiotics and quickly disintegrate in the pH environment of the intestines to release the embedded probiotics, and can meet requirements for subsequent in vivo animal evaluations.

DETAILED DESCRIPTION

The solutions of the present application are further described below through specific examples. Those skilled in the art should understand that the examples described herein are merely used for a better understanding of the present application and should not be construed as specific limitations to the present application.

Specific *Lactobacillus acidophilus* and *Bifidobacterium* strains were used in the examples of the present application, but those skilled in the art should understand that any other *Lactobacillus acidophilus* and *Bifidobacterium* strains can also be used to implement the present application. *Lactobacillus acidophilus* and *Bifidobacterium* are not specifically limited.

Example 1

In this example, a *Lactobacillus acidophilus*-loaded microcapsule was prepared by the following method:

(1) sodium alginate was dissolved in normal saline to prepare a sodium alginate solution with a concentration of 2 wt %;

(2) a solution of *Lactobacillus acidophilus* (acquired from the Fermented Food and Microbial Resources Development and Research Laboratory (5) of Tianjin University of Science and Technology) was mixed with the sodium alginate solution and stirred slowly to make them evenly mixed into a suspension, where the *Lactobacillus acidophilus* solution was added in an amount of $10^9$ CFU/mL;

(3) the suspension in step (2) was sprayed into a 1 mol/L calcium chloride solution through a nozzle of a spray dryer at a gas velocity of 500 L/h and slowly stirred, and droplets were cured to form microcapsules, where the feed rate of the spray dryer was set to 2 mL/min; and (4) the microcapsules were washed by centrifugation to remove excess calcium chloride and uncured droplets, and the prepared microcapsules were collected, suspended and stored in normal saline.

Figure 1:
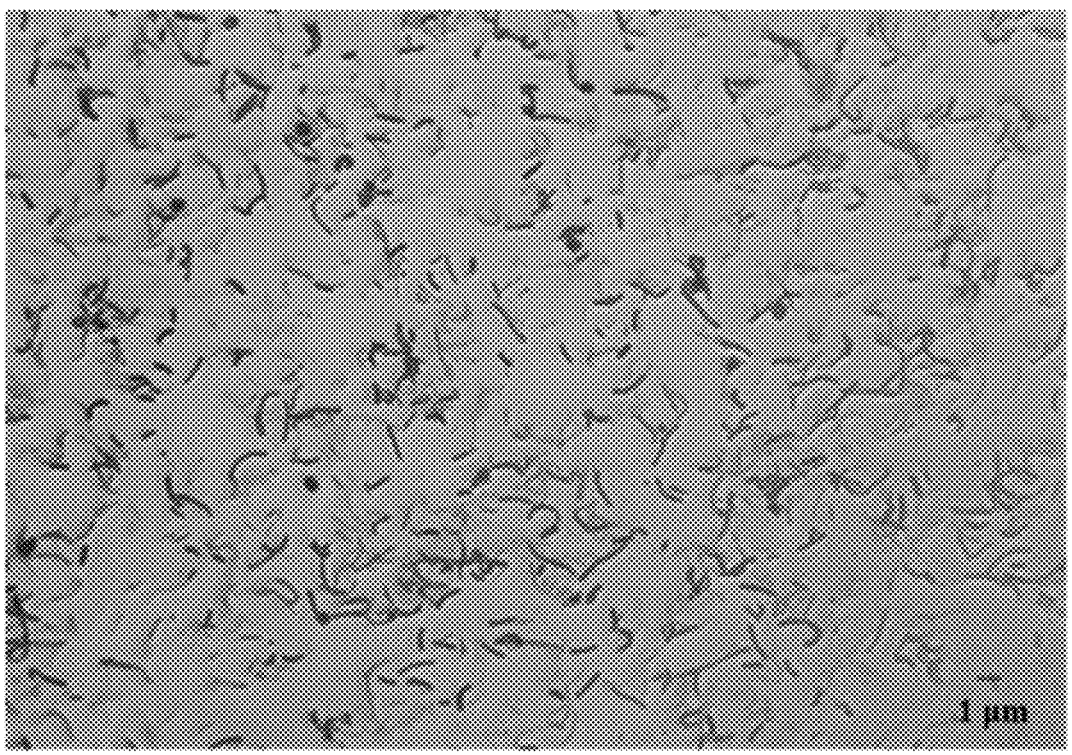
FIG. 1 is a diagram illustrating the characterization of *Lactobacillus acidophilus* under an optical microscope.
Figure 2:
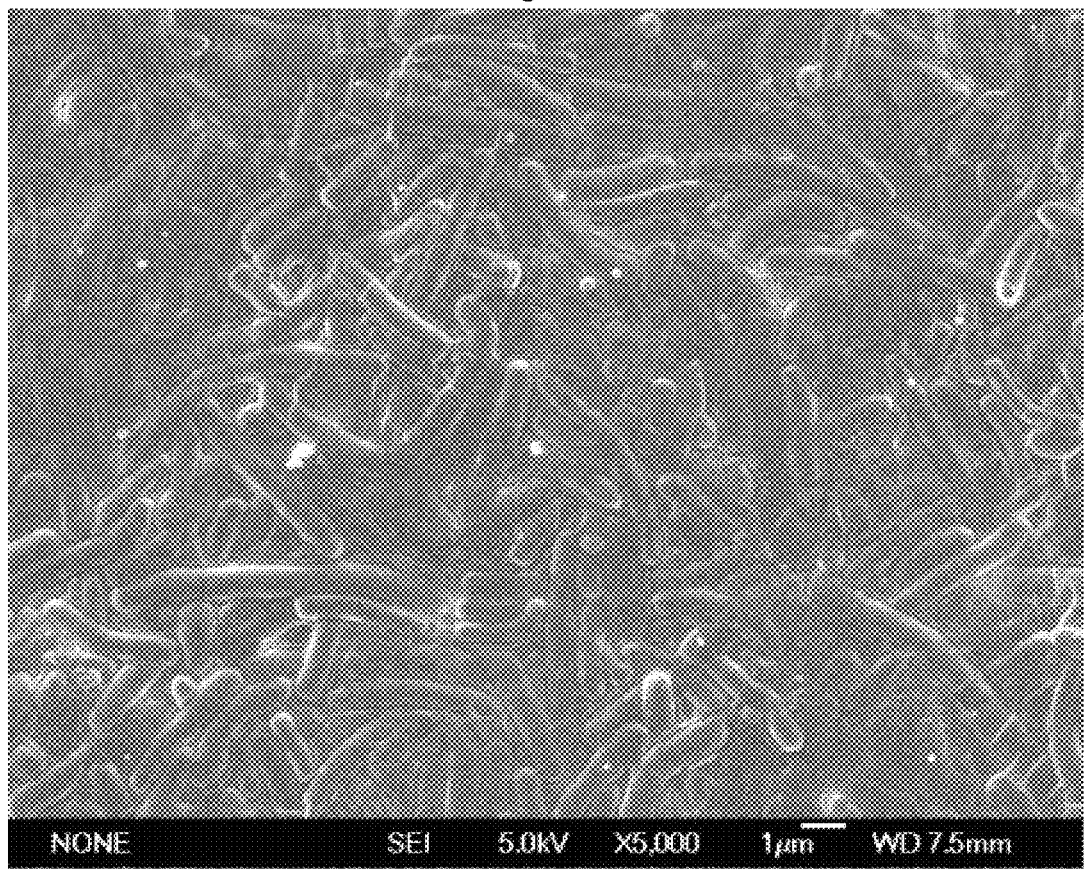
FIG. 2 is a diagram illustrating the characterization of *Lactobacillus acidophilus* under a scanning electron microscope.

The preparations and detection of *Lactobacillus acidophilus* were performed as follows:

The morphology of *Lactobacillus acidophilus* was observed with an optical microscope and a scanning electron microscope. The characterization of *Lactobacillus acidophilus* under the optical microscope is shown in FIG. 1, and the characterization of *Lactobacillus acidophilus* under the scanning electron microscope is shown in FIG. 2. *Lactobacillus acidophilus* was identified by a Gram staining method. The result in FIG. 1 shows that *Lactobacillus acidophilus* embedded is gram-positive bacteria. The morphology of *Lactobacillus acidophilus* was observed with the scanning electron microscope. FIG. 2 shows the morphology of *Lactobacillus acidophilus* amplified 5,000 times, and the result shows that *Lactobacillus acidophilus* is rod-shaped bacteria, where the rod has round ends, a length of about 2-3 μm, and a cross-sectional diameter of about 600 nm.

Example 2

In this example, a *Lactobacillus acidophilus*-loaded microcapsule was prepared by the following method:
(1) sodium alginate was dissolved in normal saline to prepare a sodium alginate solution with a concentration of 0.5 wt %;
(2) a solution of *Lactobacillus acidophilus* (acquired from the Fermented Food and Microbial Resources Development and Research Laboratory (5) of Tianjin University of Science and Technology) was mixed with the sodium alginate solution and stirred slowly to make them evenly mixed into a suspension, where the *Lactobacillus acidophilus* solution was added in an amount of $10^8$ CFU/mL;
(3) the suspension in step (2) was sprayed into a 0.5 mol/L calcium chloride solution through a nozzle of a spray dryer at a gas velocity of 450 L/h and slowly stirred, and droplets were cured to form microcapsules, where the feed rate of the spray dryer was set to 1 mL/min; and
(4) the microcapsules were washed by centrifugation to remove excess calcium chloride and uncured droplets, and the prepared microcapsules were collected, suspended and stored in normal saline.

The preparations and detection of *Lactobacillus acidophilus* were the same as those in Example 1.

Example 3

In this example, a *Lactobacillus acidophilus*-loaded microcapsule was prepared by the following method:
(1) sodium alginate was dissolved in normal saline to prepare a sodium alginate solution with a concentration of 3 wt %;
(2) a solution of *Lactobacillus acidophilus* (acquired from the Fermented Food and Microbial Resources Development and Research Laboratory (5) of Tianjin University of Science and Technology) was mixed with the sodium alginate solution and stirred slowly to make them evenly mixed into a suspension, where the *Lactobacillus acidophilus* solution was added in an amount of $10^{10}$ CFU/mL;
(3) the suspension in step (2) was sprayed into a 1.5 mol/L calcium chloride solution through a nozzle of a spray dryer at a gas velocity of 550 L/h and slowly stirred, and droplets were cured to form microcapsules, where the feed rate of the spray dryer was set to 3 mL/min; and
(4) the microcapsules were washed by centrifugation to remove excess calcium chloride and uncured droplets, and the prepared microcapsules were collected, suspended and stored in normal saline.

The preparations and detection of *Lactobacillus acidophilus* were the same as those in Example 1.

Example 4

In this example, a *Lactobacillus acidophilus*-loaded microcapsule was prepared by the following method:
(1) sodium alginate was dissolved in normal saline to prepare a sodium alginate solution with a concentration of 2 wt %;
(2) a solution of *Lactobacillus acidophilus* (acquired from the Fermented Food and Microbial Resources Development and Research Laboratory (5) of Tianjin University of Science and Technology) was mixed with the sodium alginate solution and stirred slowly to make them evenly mixed into a suspension, where the *Lactobacillus acidophilus* solution was added in an amount of $10^{11}$ CFU/mL;
(3) the suspension in step (2) was sprayed into a 1 mol/L calcium chloride solution through a nozzle of a spray dryer at a gas velocity of 500 L/h and slowly stirred, and droplets were cured to form microcapsules, where the feed rate of the spray dryer was set to 2 mL/min; and
(4) the microcapsules were washed by centrifugation to remove excess calcium chloride and uncured droplets, and the prepared microcapsules were collected, suspended and stored in normal saline.

The preparations and detection of *Lactobacillus acidophilus* were the same as those in Example 1.

Example 5

In this example, a *Bifidobacterium*-loaded microcapsule was prepared by the following method:
(1) sodium alginate was dissolved in normal saline to prepare a sodium alginate solution with a concentration of 2 wt %;

(2) a solution of *Bifidobacterium* (acquired from Tianjin Chr. Hansen Food Ingredient Co., Ltd.) was mixed with the sodium alginate solution and stirred slowly to make them evenly mixed into a suspension, where the *Bifidobacterium* solution was added in an amount of $10^{11}$ CFU/mL;

(3) the suspension in step (2) was sprayed into a 1 mol/L calcium chloride solution through a nozzle of a spray dryer at a gas velocity of 500 L/h and slowly stirred, and droplets were cured to form microcapsules, where the feed rate of the spray dryer was set to 2 mL/min; and (4) the microcapsules were washed by centrifugation to remove excess calcium chloride and uncured droplets, and the prepared microcapsules were collected, suspended and stored in normal saline.

Comparative Example 1

The preparation method of this comparative example was the same as that of Example 1, except that the salt solution was sprayed in step (3) at a gas velocity of 300 L/h, and the feed rate of the spray dryer was 5 mL/min.

Comparative Example 2

The preparation method of this comparative example was the same as that of Example 1, except that the ion solution was sprayed in step (3) at a gas velocity of 600 L/h, and the feed rate of the spray dryer was 5 mL/min.

Comparative Example 3

The preparation method of this comparative example was the same as that of Example 1, except that the salt solution was sprayed in step (3) at a gas velocity of 300 L/h, and the feed rate of the spray dryer was 0.5 mL/min.

Comparative Example 4

The preparation method of this comparative example was the same as that of Example 1, except that the ion solution was sprayed in step (3) at a gas velocity of 600 L/h, and the feed rate of the spray dryer was 0.5 mL/min.

Comparative Example 5

The preparation method of this comparative example was the same as that of Example 1, except that in step (1), the mixture of sodium alginate and modified starch was dissolved in normal saline at a mass ratio of 1:1 to prepare a mixed solution of sodium alginate and starch.

Test Example 1

Measurement of the Particle Sizes of the Microcapsules

Figure 5:
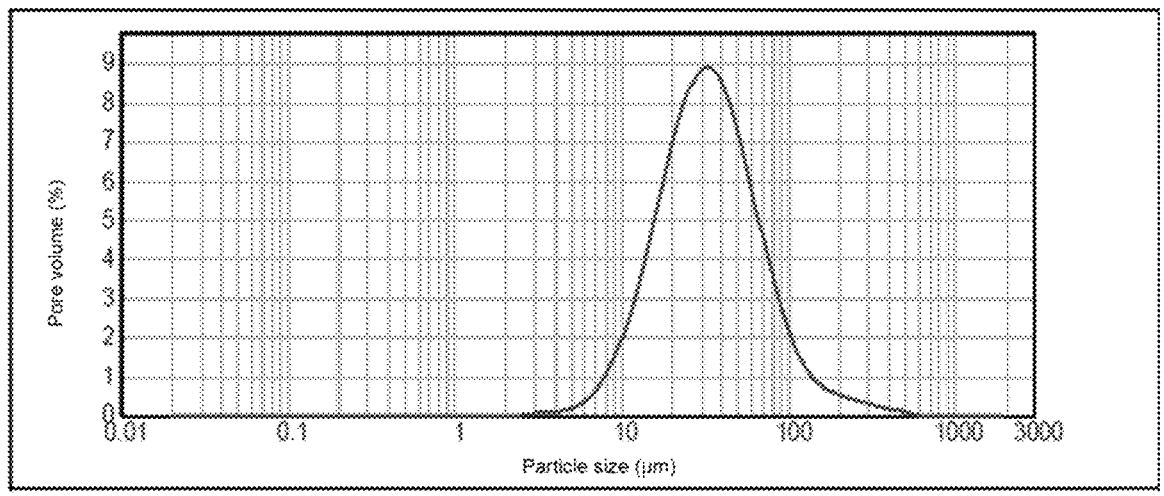
FIG. 5 is a diagram illustrating the particle size and particle size distribution of the *Lactobacillus acidophilus*-loaded microcapsule prepared in Example 1.

The probiotic-loaded microcapsules prepared in Examples 1 to 5 and the microcapsules prepared in Comparative Examples 1 to 5 were re-suspended in normal saline. After ultrasonically dispersed, these microcapsules were dripped into the sample pool of a laser particle size analyzer to measure volume-weighted mean sizes (d4,3) and particle size distributions (span). The particle sizes and particle size distributions of the microcapsules were measured with the laser particle size analyzer. The particle size and particle size distribution of the *Lactobacillus acidophilus*-loaded microcapsule prepared in Example 1 is shown in FIG. 5. The mean particle sizes of the probiotic-loaded microcapsules prepared in Examples 1 to 5 and the microcapsules prepared in Comparative Examples 1 to 5 are shown in Table 1.

TABLE 1

| Item | Mean particle size (μm) |
| --- | --- |
| Example 1 | 31.68 |
| Example 2 | 35.26 |
| Example 3 | 28.75 |
| Example 4 | 33.29 |
| Example 5 | 34.12 |
| Comparative Example 1 | 65.78 |
| Comparative Example 2 | 49.26 |
| Comparative Example 3 | 52.18 |
| Comparative Example 4 | 41.26 |
| Comparative Example 5 | 45.36 |

It can be seen from test data in Table 1 that the particle sizes of the probiotic-loaded microcapsules prepared in Examples 1 to 5 range from 25 μm to 40 μm. The process of the present application can control the capsule size and obtain microcapsules with small particle sizes, which are convenient for human bodies to absorb, thereby improving the overall performance of microcapsules. It shows that, by preparing a microcapsule using sodium alginate as the wall material of the microcapsule and using a spraying method in conjunction with an ion curing method, through synergistic effects between these two methods, the method of the present application allows the microcapsule to have a good spherical shape, a small particle size, and good dispersibility, and meet requirements for subsequent in vivo animal evaluations.

Test Example 2

Test of Embedding Rates

The probiotic-loaded microcapsules prepared in Examples 1 to 5 and the microcapsules prepared in Comparative Examples 1 to 5 were tested for embedding rates by a test method. The embedding rates of the probiotic-loaded microcapsules prepared in Examples 1 to 5 and the microcapsules prepared in Comparative Examples 1 to 5 are shown in Table 2.

TABLE 2

| Item | Embedding rate (%) |
| --- | --- |
| Example 1 | 77.96 |
| Example 2 | 75.48 |
| Example 3 | 75.26 |
| Example 4 | 79.77 |
| Example 5 | 78.66 |
| Comparative Example 1 | 60.65 |
| Comparative Example 2 | 70.28 |
| Comparative Example 3 | 66.72 |
| Comparative Example 4 | 71.63 |
| Comparative Example 5 | 78.26 |

It can be seen from test data in Table 2 that the embedding rates of the probiotic-loaded microcapsules prepared in Examples 1 to 5 are above 75%, which fully indicates that the process of the present application, by controlling the gas velocity at which a wall material suspension containing core materials is sprayed and the feed rate of a spray device during the formation of microcapsules, can further improve the embedding rate of microcapsules, meeting requirements for subsequent in vivo animal evaluations.

Test Example 3

Microscopic Observation and pH Sensitivity Test of Microcapsules

Figure 3:
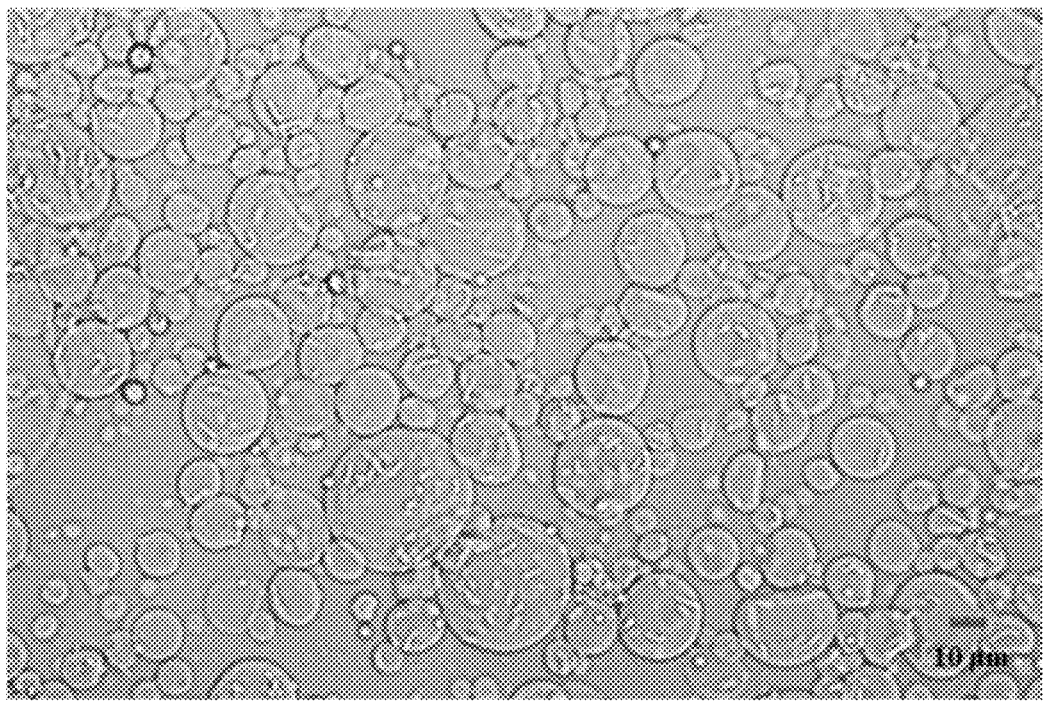
FIG. 3 is a diagram illustrating the characterization of the *Lactobacillus acidophilus*-loaded microcapsule prepared in Example 1 under an optical microscope.
Figure 4:
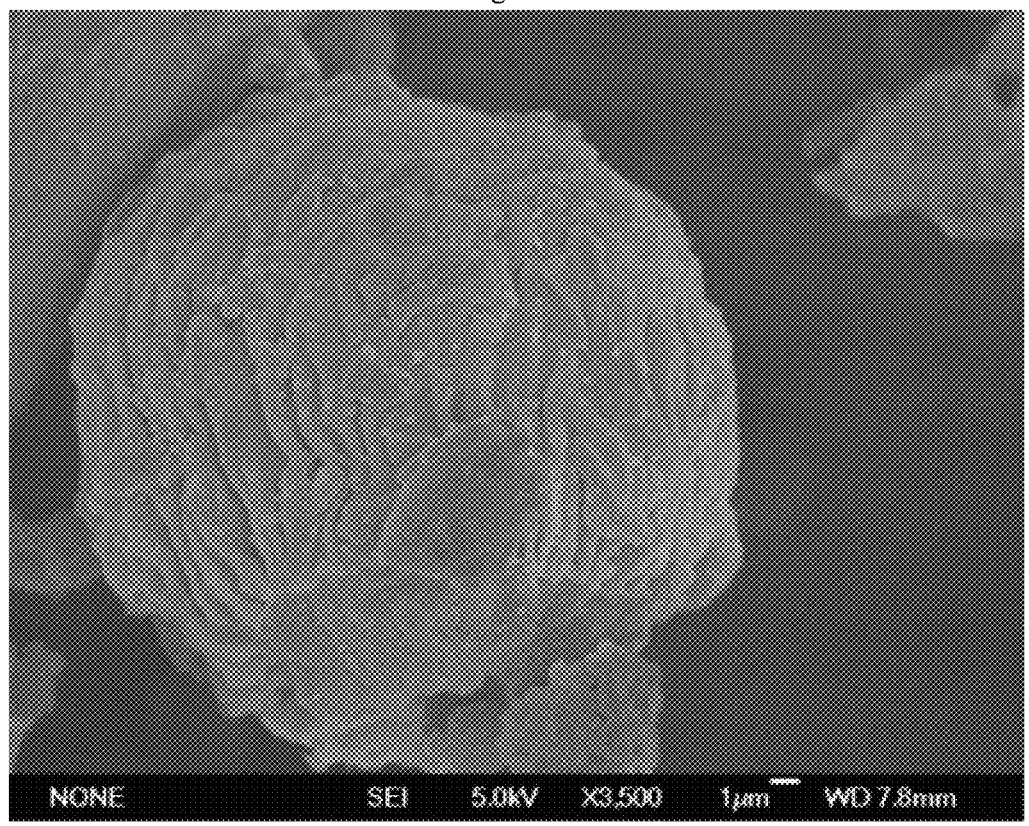
FIG. 4 is a diagram illustrating the characterization of the *Lactobacillus acidophilus*-loaded microcapsule prepared in Example 1 under a scanning electron microscope.

The morphology of the *Lactobacillus acidophilus*-loaded microcapsule was observed with an optical microscope and a scanning electron microscope (microscope model: JEOL (JEM-6700F)), and the results are shown in FIGS. 3 and 4. The morphology of the microcapsule was observed, photographed and recorded by use of the optical microscope with a shooting function. The characterization of the *Lactobacillus acidophilus*-loaded microcapsule prepared in Example 1 under the optical microscope is shown in FIG. 3. The specific process was as follows: a small amount of sample was dropped with a dropper on a glass slide and gently covered with a cover glass; an appropriate field of view was found under a low-power lens, then a high-power lens was switched to for observing the morphology of the microcapsule; the state of the sample was photographed and recorded with a WV-CP230/G camera; and the quality of the microcapsule was primarily evaluated through morphological observation. It can be seen from the microscopic photograph in FIG. 3 that many rod-shaped bacteria are embedded in the microcapsules, which indicates that the microcapsules have a relatively good effect of embedding bacteria. The morphology of the *Lactobacillus acidophilus*-loaded microcapsule was observed with the scanning electron microscope. The characterization of the *Lactobacillus acidophilus*-loaded microcapsule prepared in Example 1 under the scanning electron microscope is shown in FIG. 4. It can be seen from the morphology of the microcapsule in FIG. 4 that there are rod-shaped bacteria on the surface of the microcapsule, which indicates that the microcapsule can embed a large amount of bacterium particles.

Figure 6A:
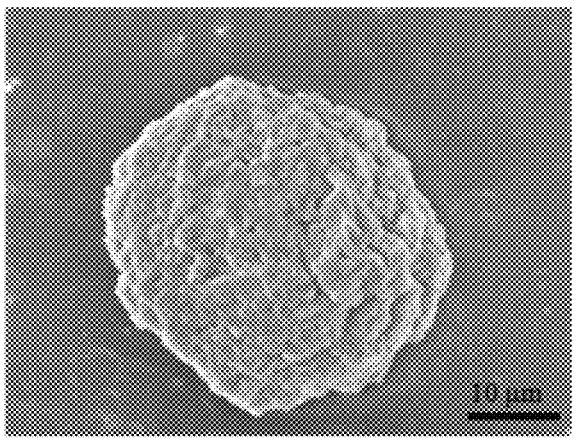
FIG. 6A illustrates the surface morphology of the *Lactobacillus acidophilus*-loaded microcapsule prepared in Example 1 in an environment where pH=1.2.
Figure 6B:
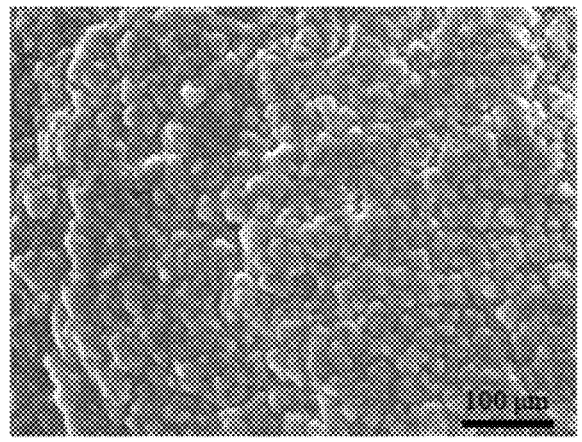
FIG. 6B is a partial enlarged view of the surface morphology of the *Lactobacillus acidophilus*-loaded microcapsule prepared in Example 1 in an environment where pH=1.2.
Figure 6C:
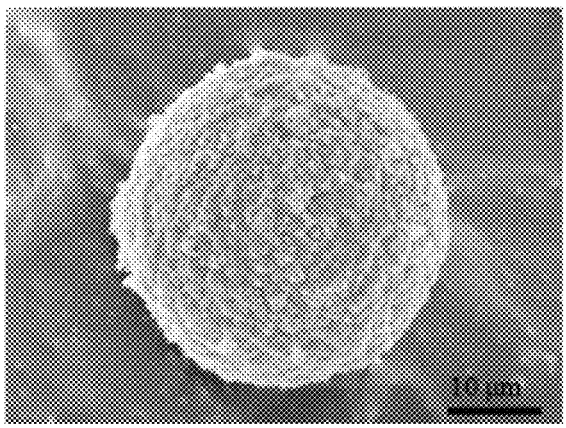
FIG. 6C illustrates the surface morphology of the *Lactobacillus acidophilus*-loaded microcapsule prepared in Example 1 in an environment where pH=6.8.
Figure 6D:
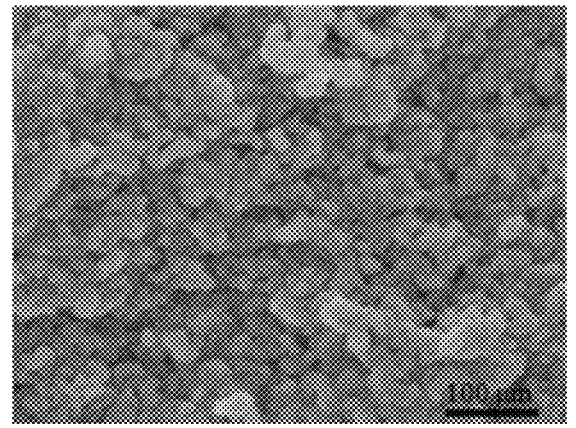
FIG. 6D is a partial enlarged view of the surface morphology of the *Lactobacillus acidophilus*-loaded microcapsule prepared in Example 1 in an environment where pH=6.8.
Figure 6E:
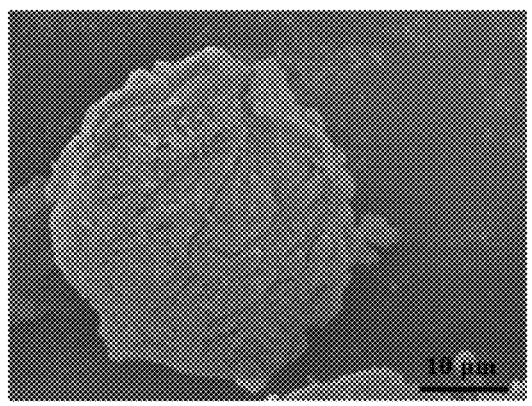
FIG. 6E illustrates the surface morphology of the *Lactobacillus acidophilus*-loaded microcapsule prepared in Comparative Example 5 in an environment where pH=1.2.
Figure 6F:
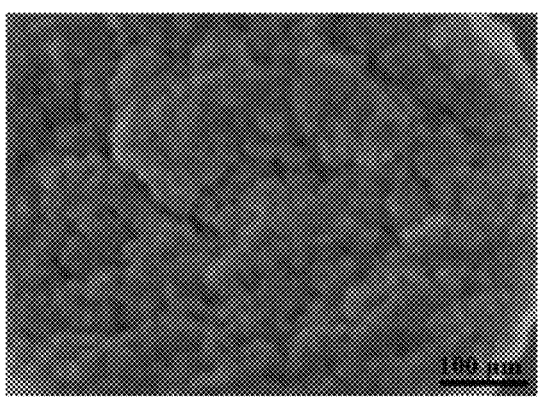
FIG. 6F is a partial enlarged view of the surface morphology of the *Lactobacillus acidophilus*-loaded microcapsule prepared in Comparative Example 5 in an environment where pH=1.2.
Figure 6G:
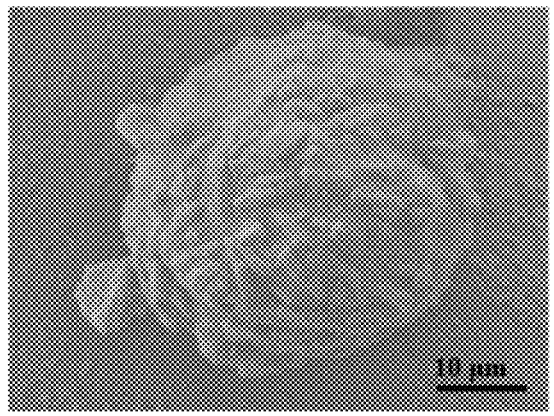
FIG. 6G illustrates the surface morphology of the *Lactobacillus acidophilus*-loaded microcapsule prepared in Comparative Example 5 in an environment where pH=6.8.
Figure 6H:
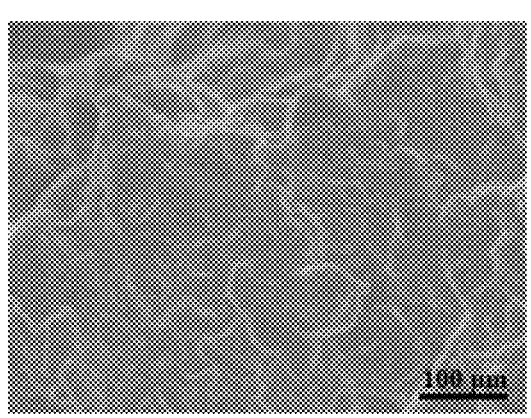
FIG. 6H is a partial enlarged view of the surface morphology of the *Lactobacillus acidophilus*-loaded microcapsule prepared in Comparative Example 5 in an environment where pH=6.8.

The surface morphology of the microcapsules was observed under different pH conditions with the electron microscope: the surface morphology of the *Lactobacillus acidophilus*-loaded microcapsule prepared in Example 1 in an environment where pH=1.2 and a partial enlarged view thereof are shown in FIGS. 6A and 6B; the surface morphology of the *Lactobacillus acidophilus*-loaded microcapsule prepared in Example 1 in an environment where pH=6.8 and a partial enlarged view thereof are shown in FIGS. 6C and 6D; the surface morphology of the *Lactobacillus acidophilus*-loaded microcapsule prepared in Comparative Example 5 in an environment where pH=1.2 and a partial enlarged view thereof are shown in FIGS. 6E and 6F; and the surface morphology of the *Lactobacillus acidophilus*-loaded microcapsule prepared in Comparative Example 5 in an environment where pH=6.8 and a partial enlarged view thereof are shown in FIGS. 6G and 6H.

From the comparison of FIGS. 6A to 6H, it can be seen that, when observed under the electron microscope and under different pH conditions, the microcapsule prepared in Example 1 of the present application has a denser surface and exhibits excellent pH sensitivity under an acidic condition and thus can effectively protect probiotics, while the capsule quickly disintegrates and releases the probiotics under a weak acid condition, which is convenient for absorption in the intestines; while the capsule prepared by adding starch as the wall material in Comparative Example 5 has low pH sensitivity and large surface holes under the acidic condition and cannot effectively protect probiotics.

Test Example 4

Effect of the *Lactobacillus acidophilus*-Loaded Microcapsule Prepared in Example 1 on Intestinal Cell Proliferation BALB/C mice (albino laboratory mice) were continuously subjected to intragastric administration for 14 days and then dissected. The ilea of the mice were taken, and prepared into slices. Ki-67 staining was performed using immunohistochemistry. Images were taken under a microscope.

Figure 7A:
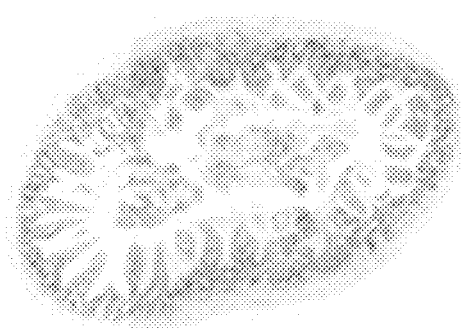
FIG. 7A is an immunohistochemistry diagram illustrating intestinal cell proliferation in a mouse administered with no drug.
Figure 7B:
FIG. 7B is a partial enlarged view of an immunohistochemistry diagram illustrating intestinal cell proliferation in a mouse administered with no drug.
Figure 7C:
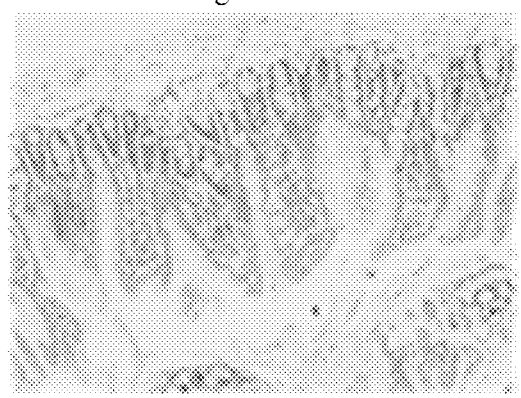
FIG. 7C is an immunohistochemistry diagram illustrating intestinal cell proliferation in a mouse on the 7th day after intragastric administration of normal saline.
Figure 7D:
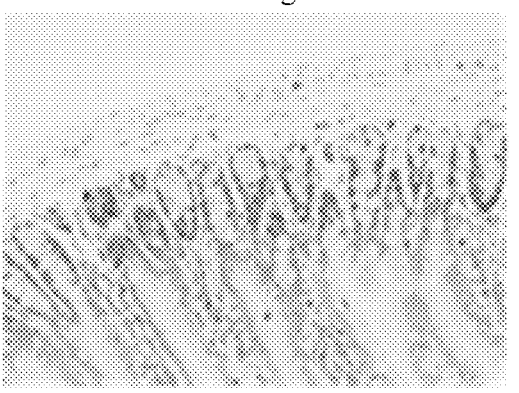
FIG. 7D is an immunohistochemistry diagram illustrating intestinal cell proliferation in a mouse on the 7th day after intragastric administration of a *Lactobacillus acidophilus* solution.
Figure 7E:
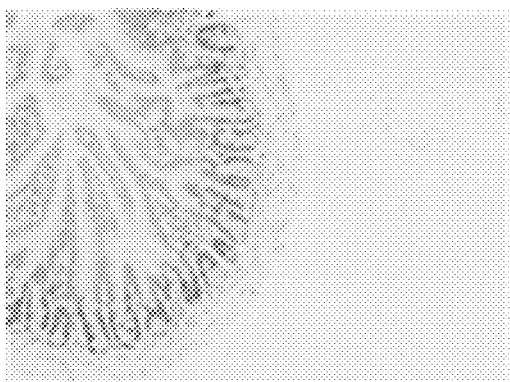
FIG. 7E is an immunohistochemistry diagram illustrating intestinal cell proliferation in a mouse on the 7th day after intragastric administration of low doses of *Lactobacillus acidophilus*-loaded microcapsules prepared in Example 1.
Figure 7F:
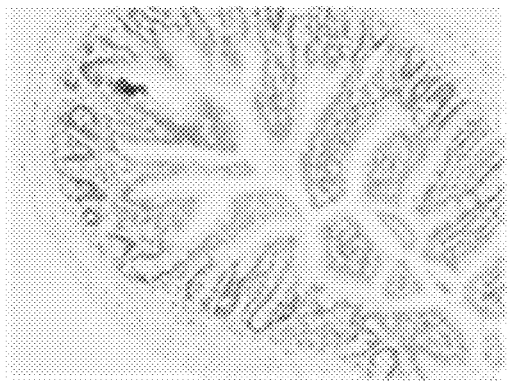
FIG. 7F is an immunohistochemistry diagram illustrating intestinal cell proliferation in a mouse on the 7th day after intragastric administration of medium doses of *Lactobacillus acidophilus*-loaded microcapsules prepared in Example 1.
Figure 7G:
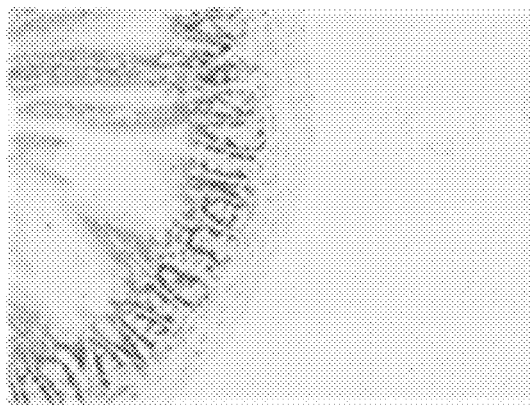
FIG. 7G is an immunohistochemistry diagram illustrating intestinal cell proliferation in a mouse on the 7th day after intragastric administration of high doses of *Lactobacillus acidophilus*-loaded microcapsules prepared in Example 1.
Figure 7H:
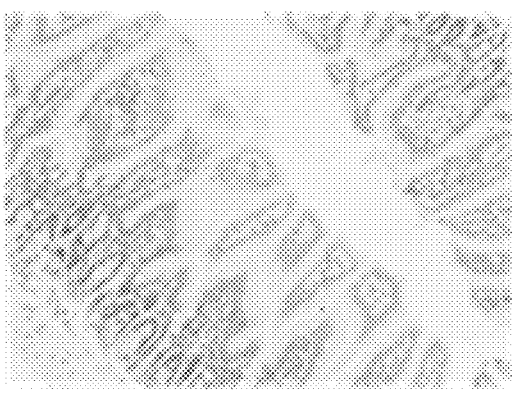
FIG. 7H is an immunohistochemistry diagram illustrating intestinal cell proliferation in a mouse on the 14th day after intragastric administration of normal saline.
Figure 7I:
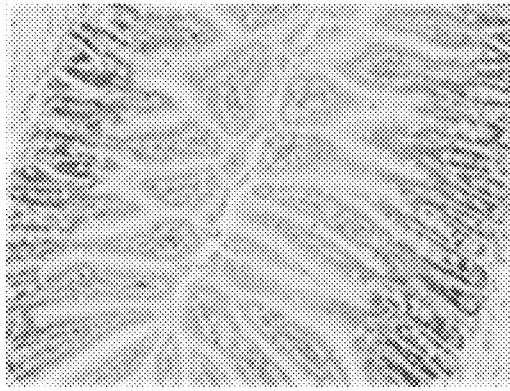
FIG. 7I is an immunohistochemistry diagram illustrating intestinal cell proliferation in a mouse on the 14th day after intragastric administration of a *Lactobacillus acidophilus* solution.
Figure 7J:
FIG. 7J is an immunohistochemistry diagram illustrating intestinal cell proliferation in a mouse on the 14th day after intragastric administration of low doses of *Lactobacillus acidophilus*-loaded microcapsules prepared in Example 1.
Figure 7K:
FIG. 7K is an immunohistochemistry diagram illustrating intestinal cell proliferation in a mouse on the 14th day after intragastric administration of medium doses of *Lactobacillus acidophilus*-loaded microcapsules prepared in Example 1.
Figure 7L:
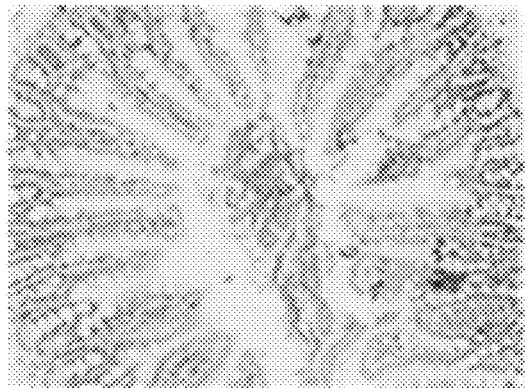
FIG. 7L is an immunohistochemistry diagram illustrating intestinal cell proliferation in a mouse on the 14th day after intragastric administration of high doses of *Lactobacillus acidophilus*-loaded microcapsules prepared in Example 1.
Figure 7M:
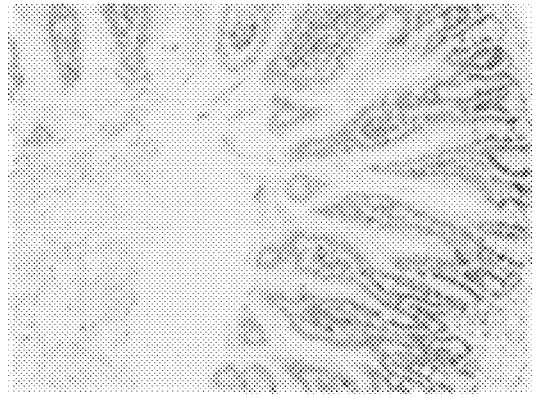
FIG. 7M is an immunohistochemistry diagram illustrating intestinal cell proliferation in a mouse on the 21st day after intragastric administration of normal saline.
Figure 7N:
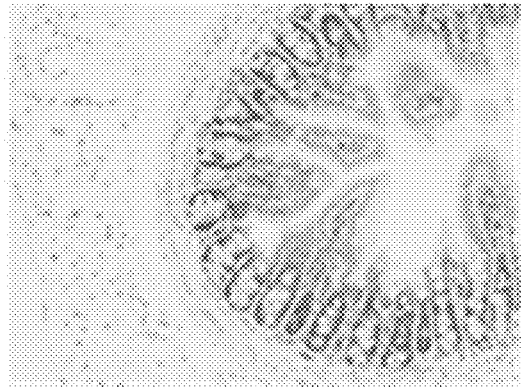
FIG. 7N is an immunohistochemistry diagram illustrating intestinal cell proliferation in a mouse on the 21st day after intragastric administration of a *Lactobacillus acidophilus* solution.
Figure 7O:
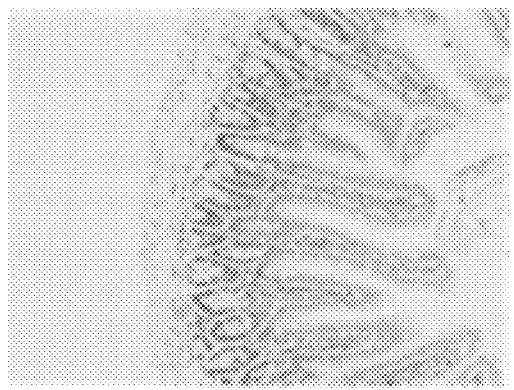
FIG. 7O is an immunohistochemistry diagram illustrating intestinal cell proliferation in a mouse on the 21st day after intragastric administration of low doses of *Lactobacillus acidophilus*-loaded microcapsules prepared in Example 1.
Figure 7P:
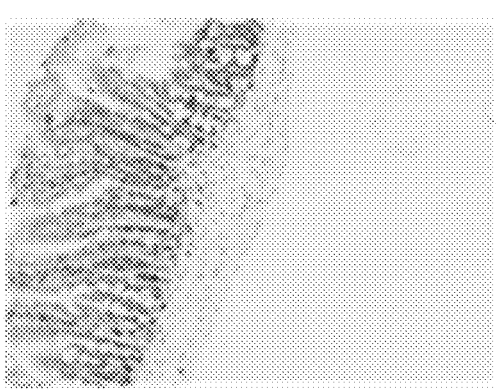
FIG. 7P is an immunohistochemistry diagram illustrating intestinal cell proliferation in a mouse on the 21st day after intragastric administration of medium doses of *Lactobacillus acidophilus*-loaded microcapsules prepared in Example 1.
Figure 7Q:
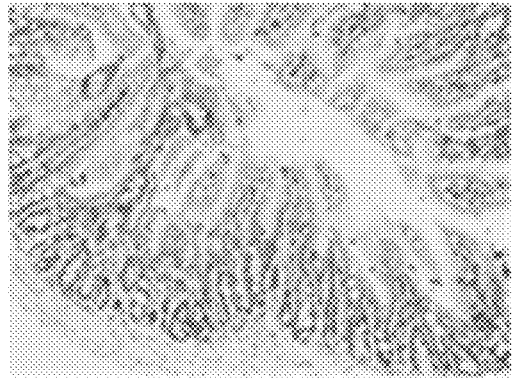
FIG. 7Q is an immunohistochemistry diagram illustrating intestinal cell proliferation in a mouse on the 21st day after intragastric administration of high doses of *Lactobacillus acidophilus*-loaded microcapsules prepared in Example 1.

The data processing and statistics of the slices were performed with a Vectra III Automated Quantitative Pathology Imaging System. The immunohistochemical situations of ileum cell proliferation in mice on days 0, 7, 14, and 21 of oral administration of normal saline, a *Lactobacillus acidophilus* solution, and low, medium and high doses of *Lactobacillus acidophilus*-loaded microcapsules (the content of bacteria in each dose of the low, medium and high doses was $10^8$ CFU, $10^9$ CFU and $10^{10}$ CFU respectively) are shown in FIGS. 7A to 7Q. It can be seen that as the number of days of administration increases, compared with the blank control group (the group intragastrically administered with normal saline), mice in the group intragastrically administered with the *Lactobacillus acidophilus* solution, and in the groups intragastrically administered with low, medium and high doses of *Lactobacillus acidophilus*-loaded microcapsules all exhibit increased proliferation of intestinal epithelial cells, but the mice administered with *Lactobacillus acidophilus*-loaded microcapsules exhibit more obvious proliferation of intestinal epithelial cells than the group intragastrically administered with the *Lactobacillus acidophilus* solution. The mice orally administered with a high dose of *Lactobacillus acidophilus*-loaded microcapsules exhibit the most obvious proliferation of intestinal epithelial cells, which indicates that the administration at a high dose of *Lactobacillus acidophilus*-loaded microcapsules has the best effect.

Figure 8A:
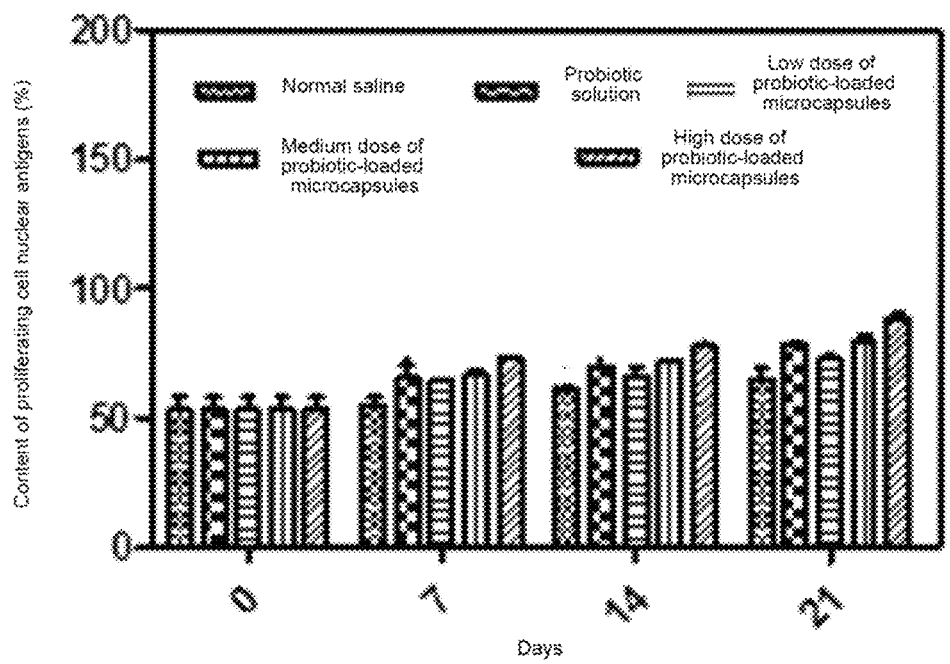
FIG. 8A is a statistical histogram of intestinal cell proliferation in mice after intragastric administration of the *Lactobacillus acidophilus*-loaded microcapsule prepared in Example 1.
Figure 8B:
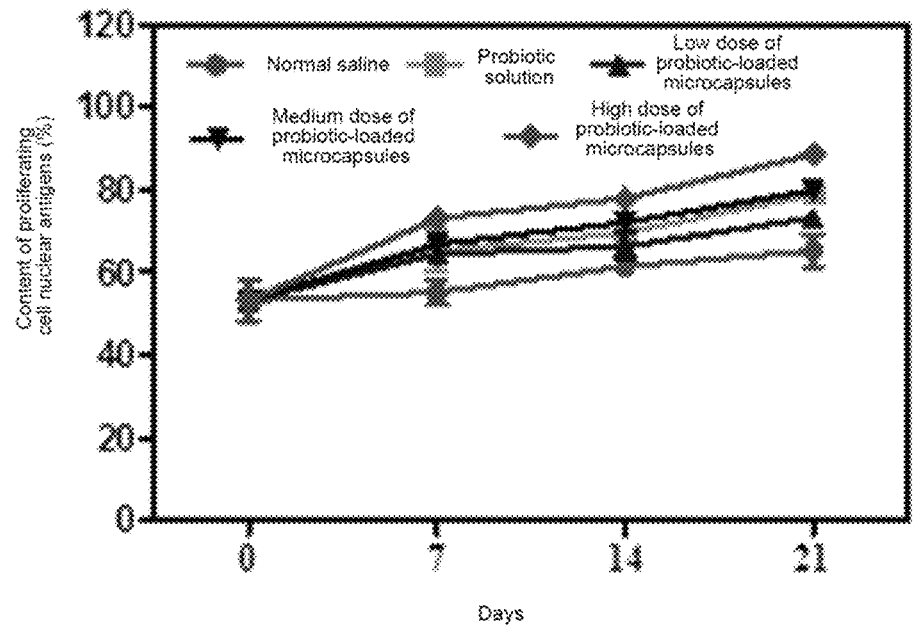
FIG. 8B illustrates statistical curves of intestinal cell proliferation in mice after the intragastric administration of the *Lactobacillus acidophilus*-loaded microcapsule prepared in Example 1.

The statistical histogram of the intestinal cell proliferation in mice intragastrically administrated with the *Lactobacillus acidophilus*-loaded microcapsule prepared in Example 1 is shown in FIG. 8A. The statistical curves of the intestinal cell proliferation in mice intragastrically administrated with the *Lactobacillus acidophilus*-loaded microcapsule prepared in Example 1 is shown in FIG. 8B. Compared with the blank control group (the group intragastrically administered with normal saline), the oral administration of low, medium and high doses of *Lactobacillus acidophilus*-loaded microcapsules can significantly promote the proliferation of intestinal epithelial cells in mice. On the 7th, 14th and 21st days of administration, compared with the blank control group, the group intragastrically administered with the *Lactobacillus acidophilus* solution, and the groups of the low, medium and high doses of *Lactobacillus acidophilus*-loaded microcapsules all exhibit significant differences in terms of proliferation of intestinal epithelial cells in mice, which indicates that the administration of *Lactobacillus acidophilus*-loaded microcapsules has a significant effect.

Test Example 5

Figure 9:
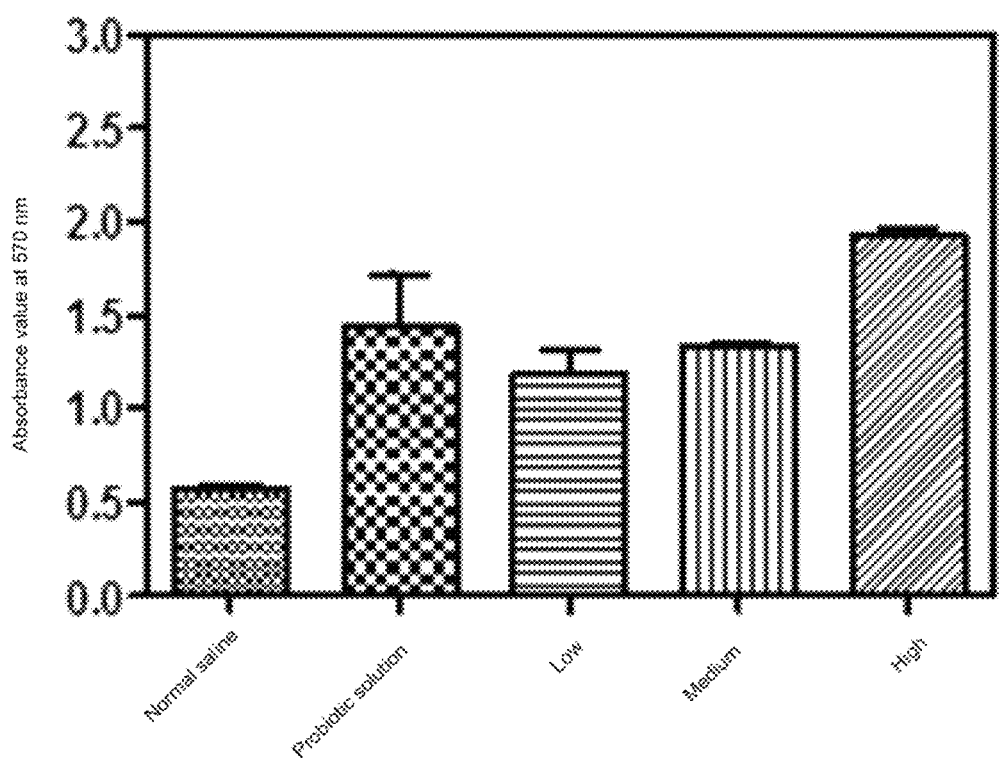
FIG. 9 is a statistical histogram illustrating an effect of the *Lactobacillus acidophilus*-loaded microcapsule prepared in Example 1 on the activity of small intestinal macrophages.

Test of the Effect of a *Lactobacillus acidophilus*-Loaded Microcapsule Prepared in Example 1 on the Phagocytic Activity of Macrophages BALB/C mice were intragastrically administered with *Lactobacillus acidophilus*-loaded microcapsules for 14 days and caused to death by dislocating cervical spines. The spleens were aseptically removed to prepare spleen cell suspensions. The effect of the intragastric administration of *Lactobacillus acidophilus*-loaded microcapsules on the phagocytic activity of spleen macrophages of mice was tested. The results of the effect of the *Lactobacillus aci*- dophilus-loaded microcapsule prepared in Example 1 on the activity of small intestinal macrophages are shown in FIG. 9. The ordinate in FIG. 9 represents the absorbance value at 570 nm. This value is related to the phagocytic activity of macrophages. The larger the value, the stronger the phagocytic activity. Low, medium, and high on the abscissa represent the oral administration of low, medium and high doses of *Lactobacillus acidophilus*-loaded microcapsules respectively (the content of bacteria in each dose of the low, medium and high doses was $10^8$ CFU, $10^9$ CFU and $10^{10}$ CFU respectively). Compared with the blank control group, the oral administration of *Lactobacillus acidophilus*-loaded microcapsules can increase the phagocytic activity of mouse spleen macrophages. The phagocytic activity of mouse spleen macrophages is dose-dependent, that is, the higher the amount of bacteria contained in the microcapsules, the better the phagocytic activity of mouse spleen macrophages. Compared with the blank control group, the high doses of *Lactobacillus acidophilus*-loaded microcapsules can extremely significantly increase the phagocytic ability of mouse spleen macrophages ($p<0.001$), indicating that the *Lactobacillus acidophilus*-loaded microcapsule has the ability to activate macrophages and thus can increase the non-specific immune function of bodies.

Test Example 6

Effect of the *Lactobacillus acidophilus*-Loaded Microcapsule of Example 1 on T Lymphocyte Subpopulations Mature T lymphocytes recirculate through lymphatic vessels and peripheral blood, etc., to exert functions such as cellular immunity and immune regulation. The flow cytometry analyzer detects lymphocyte subpopulations according to different lymphocyte surface markers. Lymphocytes mainly include T lymphocytes ($CD3^+$), B lymphocytes ($CD19^+$), and NK cells ($CD16^+CD56^+$), where T lymphocytes can be further identified as helper T lymphocytes ($CD3^+CD4^+$) and inhibitory/cytotoxic T lymphocytes ($CD3^+CD8^+$).

Figure 10A:
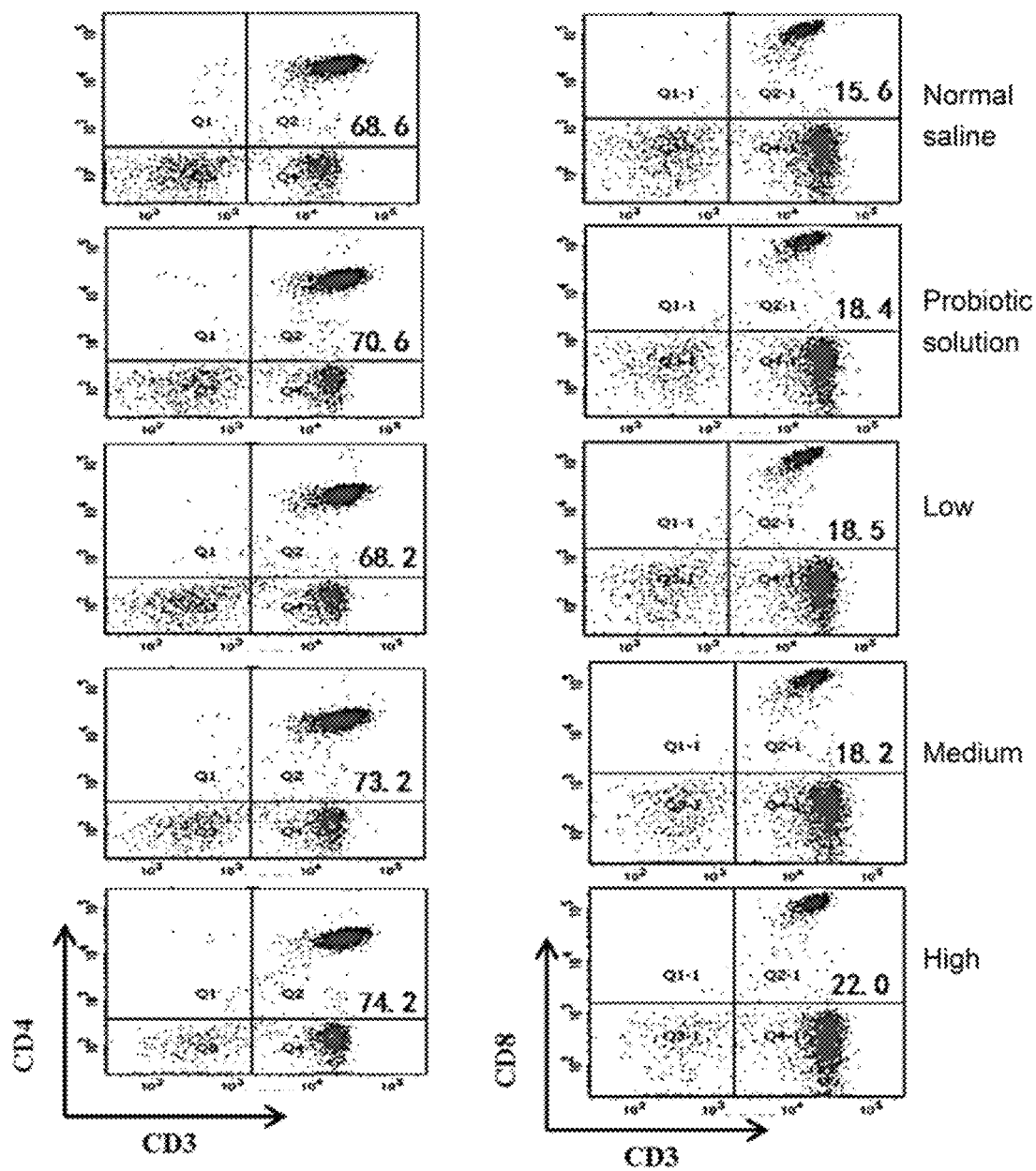
FIG. 10A is a representative flow cytometry diagram illustrating an effect of the *Lactobacillus acidophilus*-loaded microcapsule prepared in Example 1 on lymphocyte subpopulations.
Figure 10B:
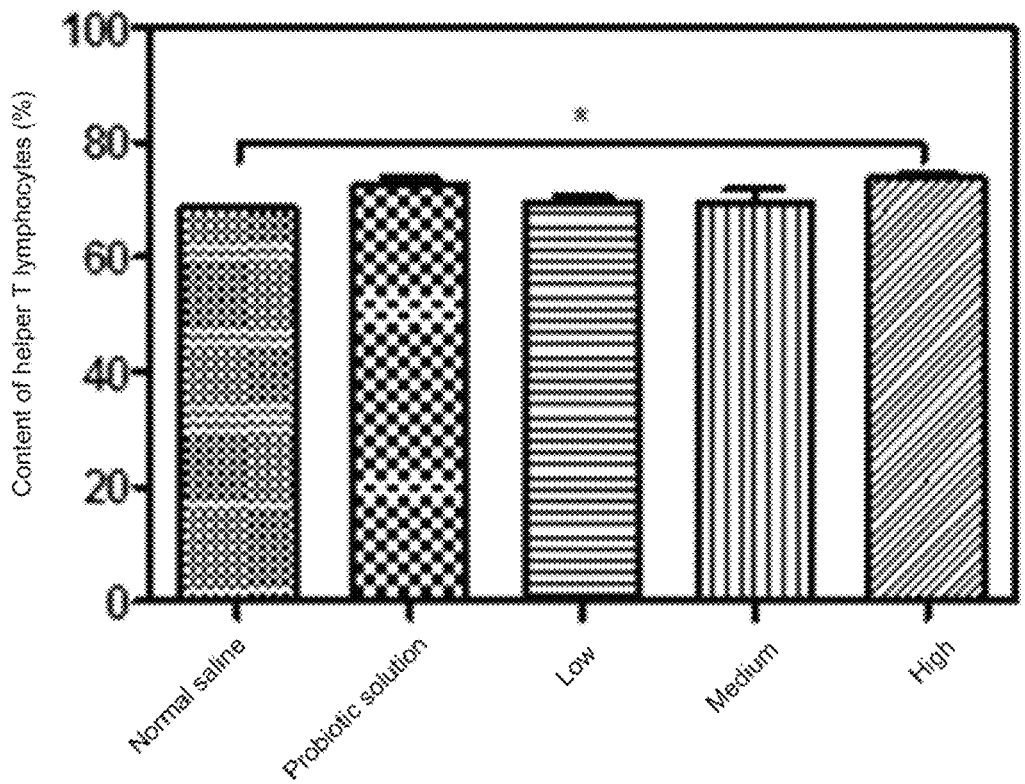
FIG. 10B is a statistical diagram illustrating an effect of the *Lactobacillus acidophilus*-loaded microcapsule prepared in Example 1 on helper T lymphocytes.
Figure 10C:
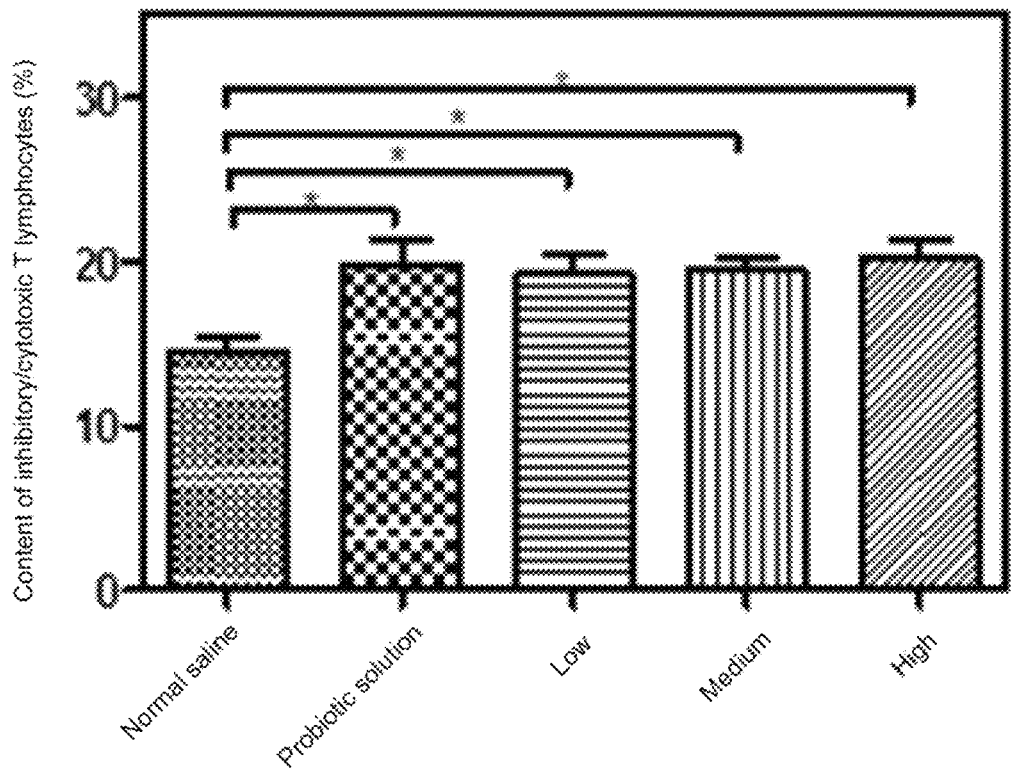
FIG. 10C is a statistical diagram illustrating an effect of the *Lactobacillus acidophilus*-loaded microcapsule prepared in Example 1 on cytotoxic T lymphocytes.

The representative flow test results of the effect of the *Lactobacillus acidophilus*-loaded microcapsule prepared in Example 1 on lymphocyte subpopulations are shown in FIG. 10A, where the abscissa and the ordinate represent the cell numbers of the corresponding cell subpopulations, respectively; and low, medium and high on the right represent the oral administration of low, medium and high doses of *Lactobacillus acidophilus*-loaded microcapsules respectively (the content of bacteria in each dose of the low, medium and high doses was $10^8$ CFU, $10^9$ CFU and $10^{10}$ CFU respectively). The effect of the *Lactobacillus acidophilus*-loaded microcapsule prepared in Example 1 on mouse helper T lymphocytes (CD3+CD4+) is shown in FIG. 10B. The effect of the *Lactobacillus acidophilus*-loaded microcapsule prepared in Example 1 on inhibitory/cytotoxic T lymphocytes ($CD3^+CD8^+$) is shown in FIG. 10C. The results show that compared with the blank control group, the BALB/C mice orally administered with *Lactobacillus acidophilus*-loaded microcapsules exhibit significantly increased contents of $CD3^+CD4^+$ and $CD3^+CD8^+$ lymphocytes among the T lymphocyte subpopulations in peripheral blood ($p<0.05$). The increase in the content of $CD4^+T$ lymphocytes is conducive to assisting in humoral immunity and mediating cellular immunity to regulate the body's immune function, and the increase in the content of $CD8^+T$ lymphocytes is conducive to improving the body's immune level.

The applicant has stated that although the processes and methods of the present application are described through the examples described above, the present application is not limited to the processes and steps described above, which means that the implementation of the present application does not necessarily depend on the processes and steps described above. It should be apparent to those skilled in the art that any improvements made to the present application, equivalent replacements of raw materials selected in the present application and additions of adjuvant ingredients thereof, and selections of specific methods, etc., all fall within the protection scope and the disclosed scope of the present application.

What is claimed is:

1. A method for preparing a probiotic-loaded microcapsule, comprising the following steps:
    (1) dissolving sodium alginate in a solvent to obtain a sodium alginate solution;
    (2) evenly mixing a probiotic with the sodium alginate solution obtained in step (1) to obtain a probiotic suspension; and
    (3) spraying the probiotic suspension obtained in step (2) into a salt solution, stirring and curing, to obtain the probiotic-loaded microcapsule,
    wherein the probiotic suspension is sprayed into the salt solution at a gas velocity of 450-550 L/h and at a feed rate of 1-3 mL/min;
    and wherein the probiotic in step (2) is selected from any one or a combination of *Lactobacillus acidophilus*, or *Bifidobacterium*, wherein the microcapsule has a particle size of 25-40 μm.

2. The method for preparing a probiotic-loaded microcapsule of claim 1, wherein the solvent in step (1) is normal saline.

3. The method for preparing a probiotic-loaded microcapsule of claim 1, wherein the sodium alginate solution in step (1) has a concentration of 0.5% to 3% by mass.

4. The method for preparing a probiotic-loaded microcapsule of claim 1, wherein the probiotic in step (2) is added in an amount of $10^8$-$10^{11}$ CFU/mL.

5. The method for preparing a probiotic-loaded microcapsule of claim 1, wherein in step (3), the probiotic suspension is sprayed into the salt solution through a nozzle of a spray dryer.

6. The method for preparing a probiotic-loaded microcapsule of claim 1, wherein the salt solution is a calcium salt solution.

7. The method for preparing a probiotic-loaded microcapsule of claim 6, wherein the calcium salt solution has a concentration of 0.5-1.5 mol/L.

8. The method for preparing a probiotic-loaded microcapsule of claim 6, wherein the calcium salt solution comprises any one or a combination of at least two of calcium gluconate, calcium hydrogen phosphate, calcium lactate, calcium sulfate or calcium chloride.

9. The method for preparing a probiotic-loaded microcapsule of claim 6, wherein the calcium salt solution comprises any one or a combination of at least two of calcium gluconate, calcium hydrogen phosphate, calcium lactate, or calcium sulfate.

10. The method for preparing a probiotic-loaded microcapsule of claim 1, after step (3), further comprising step (4): washing the probiotic-loaded microcapsule obtained in step (3), collecting, suspending and storing the probiotic-loaded microcapsule in a solvent.

11. The method for preparing a probiotic-loaded microcapsule of claim 10, wherein the probiotic-loaded microcapsule is washed by centrifugation; and
the solvent in step (4) is normal saline.

12. The method for preparing a probiotic-loaded microcapsule of claim 1, wherein the method comprises:
(1) dissolving sodium alginate in a solvent to obtain a sodium alginate solution with a concentration of 0.5% to 3% by mass;
(2) evenly mixing a probiotic with the sodium alginate solution obtained in step (1) to obtain a probiotic suspension, wherein the probiotic is added in an amount of $10^8$-$10^{11}$ CFU/mL;
(3) spraying the probiotic suspension obtained in step (2) into a calcium salt solution through a nozzle of a spray dryer at a gas velocity of 450-550 L/h, stirring and curing, to obtain the probiotic-loaded microcapsule, wherein the calcium salt solution has a concentration of 0.5-1.5 mol/L, and the feed rate of the spray dryer is 1-3 mL/min; and
(4) washing the probiotic-loaded microcapsule obtained in step (3) by centrifugation, collecting, suspending and storing the probiotic-loaded microcapsule in normal saline.

13. The method for preparing a probiotic-loaded microcapsule of claim 1, wherein the solvent in step (1) is water or an aqueous sodium chloride solution.

14. The method for preparing a probiotic-loaded microcapsule of claim 13, wherein the aqueous sodium chloride solution has a concentration of 0.85% to 0.9% by mass.

15. The method for preparing a probiotic-loaded microcapsule of claim 1, wherein the microcapsule has a particle size of 30-35 μm.

* * * * *